United States Patent
Leonard

(12) 
(10) Patent No.: US 6,489,494 B1
(45) Date of Patent: Dec. 3, 2002

(54) USES OF KOMBIC ACID AS AN ANTIOXIDANT

(76) Inventor: Edward C. Leonard, 5100 Poplar Ave., Suite 2700, Memphis, TN (US) 38137

( * ) Notice: Subject to any disclaimer, the term of this patent is extended or adjusted under 35 U.S.C. 154(b) by 0 days.

(21) Appl. No.: 09/910,152

(22) Filed: Jul. 19, 2001

(51) Int. Cl.$^7$ .................................................. C11B 1/00
(52) U.S. Cl. .................. 554/13; 584/7; 584/8; 584/12; 584/218; 514/547; 514/559
(58) Field of Search ............... 554/218, 7, 8, 554/12, 13; 514/559, 547

(56) References Cited

U.S. PATENT DOCUMENTS 5,674,900 A * 10/1997 Ubillas et al. ............... 514/557

OTHER PUBLICATIONS

Lok, C.M., Groenewegen, A., Stroink, B.A., and Ward, J.P., *Phytochemistry*, vol. 22, No. 9, pp. 1973–1976, 1983.

\* cited by examiner

*Primary Examiner*—Deborah D. Carr
(74) *Attorney, Agent, or Firm*—Wyatt, Tarrant & Combs, LLP

(57) ABSTRACT

This invention provides a novel antioxidant, kombic acid or a derivative thereof, obtained from crude kombo butter suitable for preventing oxidation of various organic materials. In particular, the invention relates to the use of kombic acid as an antioxidant in the stabilization of human and animal foods against rancidity, color and odor development; as an antioxidant for use in dietary supplements and other human and animal health formulations; as a stabilizer in cosmetic and other personal care applications; and in the stabilization of plastics against oxidative degradation. The present invention further encompasses a method of preparation of said kombic acid by alcohol extraction or supercritical fluid extraction from crude kombo butter.

33 Claims, 1 Drawing Sheet

The Chemical Structure of Kombic Acid

Figure 1: The Chemical Structure of Kombic Acid
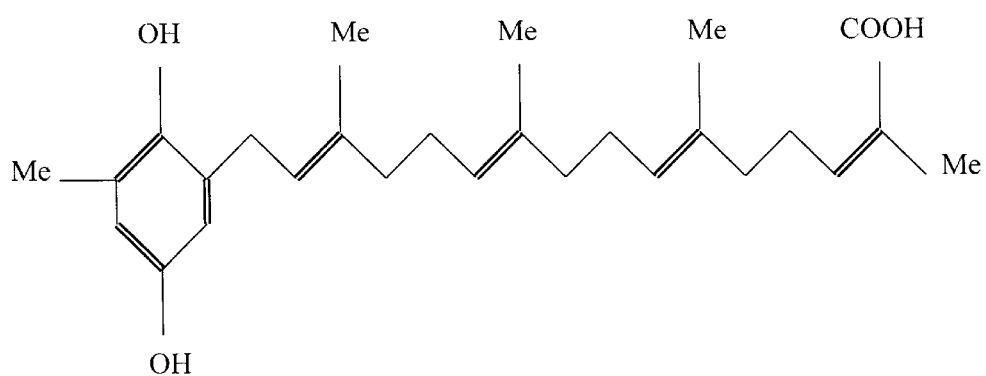
Figure 2: The Chemical Structure of Useful Derivatives of Kombic Acid where R' can be acyl moieties such as acetyl, butyryl, succinyl, nicotinyl (or hydrogen for one R') and R" can be alkyl moieties such as methyl, ethyl and longer alkyl chains.
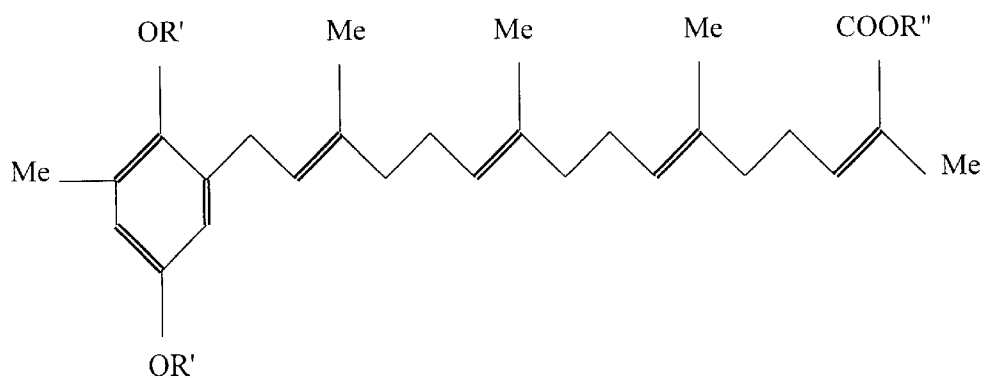

USES OF KOMBIC ACID AS AN ANTIOXIDANT

CROSS-REFERENCE TO RELATED APPLICATIONS

None

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to the polyisoprenoic natural terpenoid with the common name kombic acid and the chemical name 16(2', 5'-dihydroxy-3'-methylphenyl)-2,6,10,14-tetramethyl-2,6,10,14-hexadecatetraenoic acid. More particularly, the present invention relates to the use of kombic acid and its derivatives as an antioxidant in the stabilization of human and animal foods against the development of rancidity and color and odor development; as an antioxidant in dietary supplements and other human and animal health formulations; as a stabilizer in cosmetic and other personal care applications; and as a stabilizer against oxidative degradation in plastics. The present invention also encompasses improved methods of isolating kombic acid and its derivatives.

2. General Background of the Invention

Fats and oils are water-insoluble, hydrophobic substances of vegetable, land animal or marine animal origin that consist mostly of glyceryl esters of fatty acids, called triglycerides. Their structure is shown below, where $R_1$, $R_2$, and $R_3$ can be the same or different —$(CH_2)_xCH_3$ chains, with x being an odd number of 5 or greater.

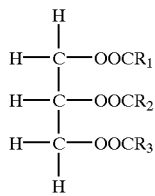

The chains (the Rs) may be completely saturated with respect to hydrogen or have one or more double bonds. When $R_1$ is seventeen carbons with no double bonds, the chain is called stearic; in this case there are thirty-five hydrogen atoms attached to the seventeen carbons. With one double bond the same carbon-length chain is called oleic and there are thirty-three attached hydrogen atoms. When there is more than one double bond, the fatty acids are polyunsaturated. Linoleic acid, for example, has eighteen carbons atoms and two double bonds, and linolenic acid has three double bonds and eighteen carbon atoms.

There are roughly 100 million metric tons of fats and oils consumed globally with about 80% used for human food. The balance is used as industrial oils, in animal feed, to make soap, and to produce oleochemicals, which have many industrial applications, most notably as plastics additives and food processing ingredients.

The principal fats and oils used in food are canola, soybean, palm, sunflower seed, coconut, palm kernel, sesame, olive, corn, cottonseed, edible tallow and lard. The most frequently occurring fatty acids found in these fats and oils are stearic, oleic, linoleic, linolenic, palmitic ($C_{16:0}$), palmitoleic ($C_{61:1}$), myristic($C_{14:0}$) and lauric($C_{12:0}$). The first two digits in the carbon subscript refer to carbon chain length, and the number after the colon refers to the number of double bonds in the chain.

Myristoleic acid, which has fourteen carbon atoms and one double bond in the chain has an ester derivative, cetyl myristoleate, with claimed efficacy in relieving the pain of rheumatoid arthritis and osteoarthritis[1, 2]. The myristoleic acid used to make this product up to now has been derived from beef tallow.

There are two commonly accepted reference sources with respect to published treatises on fats and oils: "Bailey's Industrial Oil and Fat Products," Fourth Edition, John Wiley & Sons, and Gunstone and Padley's, "Lipid Technologies and Applications," Marcel Dekker, Inc. In "Bailey's" there is the following discussion of sources of myristoleic acid, all based on land animal or marine animal origin.

9-Tetradecenoic (myristoleic) acid is the most common of the tetradecenoic acids, being first detected in whale oil in 1925 at about 1.4%, later in whale blubber oil, in shark liver oil, Antarctic whale oil, eel oil, and turtle oil. In 1924 it was suggested to occur in butterfat; it was found to constitute 1% of the total acids. It also occurs in goat milk fat, human milk fat, and various animal depot fats, (particularly beef tallow).

It is noteworthy that there is not the slightest reference in Bailey's to any vegetable oil sources.

Gunstone and Padley, in their well-recognized reference work mention hundreds of fatty acids but make no reference of any sort to myristoleic acid. Useful products can be obtained from myristoleic acid, most notably cetyl myristoleate, a possible remedy for alleviating the pain and inflammation of arthritis and related maladies[1, 2]. However, cetyl myristoleate based on myristoleic acid sourced from animal origins, up to now the only ostensible source, has several disadvantages:

1) Fatty acids derived from beef tallow run the risk, albeit slight, of inducing bovine spongiform encephalitis (mad-cow disease).
2) Any fatty acid sourced from land animal or marine animal origins cannot be Kosher or the Islamic equivalent, Halal.
3) Any fatty acids sourced from land animal or marine animal origins cannot be "vegetarian" or "vegetable-oil food-grade."

Myristoleic acid, however, is not exclusively sourced from non-vegetable oil origins. There is a tree that produces a nut containing a vegetable butter that is a relatively good source of myristoleic acid[3, 4, 5, 6, 7]. The fat is known as kombo butter. It comes from the seeds of Pycnanthus Kombo (Myristicaceae family) found in West Central Africa. Other compounds isolated from P. Kombo (P. Angolensis) include 2'-hydroxy-4'-7-dimethoxy isoflavone and 2'-hydroxy formonometin[8]. In addition, U.S. Pat. No. 5,674,900 00 describes the isolation and use of terpenoid quinones from the stems and leaves (not the seedfat) of P. kombo for use in treating diabetes[9].

The seedfat of P. kombo is reddish-brown and has a distinct aromatic odor. The fat also contains 20–30% of kombic acid. Kombic acid is not a fatty acid per se, rather it is a substituted fatty acid, and must be separated and removed from kombo butter in manufacturing downstream oleochemical products such as myristoleic acid. From kombo butter, the unit operations to obtain relatively pure distilled fatty acid mixtures containing appreciable levels of myristoleic acid include: 1) fat (kombo butter) saponification to split the fat and form the sodium soaps of the fatty acids, thereby separating and removing the glycerine, 2) acidulation of the sodium soaps of the fatty acids to reform the free fatty acids, and 3) molecular distillation of the crude fatty acids for purposes of purification. The cetyl esters can then be formed by conventional esterification reactions. The present invention describes the unexpected isolation, and manufacture of substituted fatty acids and substituted fatty acid derivatives from the seed fat of Pycnanthus Kombo via alcohol extraction and supercritical $CO_2$ methods and their use as antioxidants. This substituted fatty acid is kombic acid and the substituted fatty acid derivatives are derivatives of kombic acid.

BRIEF SUMMARY OF THE INVENTION

The method of the present invention provides an antioxidant and stabilizer in human and animal pharmaceuticals and dietary supplements. The method of the present invention also solves the problems of stabilization of human and animal foods against the development of rancidity, color and odor; stabilization of cosmetic and other personal care products; and the stabilization of plastics against oxidative degradation by using kombic acid, or a kombic acid derivative, as an antioxidant. In addition, the invention method solves the problem of isolating kombic acid in a highly purified form on a large scale for such use.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein:

FIG. 1 shows the chemical formula of kombic acid;

FIG. 2 shows the chemical formula of derivatives of kombic acid having the same desirable antioxidative properties as kombic acid where R' can be acyl moieties such as acetyl-, butyryl-, succinyl-, nicotinyl-, (or hydrogen for one R') and R" can be alkyl moieties such as methyl, ethyl and longer alkyl chains.

DETAILED DESCRIPTION OF THE INVENTION

The present invention provides a novel antioxidant with the common name, kombic acid. Lipids (oils and fats; triacylglycerols), whether in the human biological system or as food products, undergo oxidation. Lipid oxidation in the human body facilitates the aging process, and in particular contributes heavily to the development of coronary artery disease. Oxidation takes place more rapidly in unsaturated fatty acids than in saturated fatty acids and most rapidly in the polyunsaturated fatty acids such as those contained (as fatty acid acylglycerols) in fish oils, linseed oil and soybean oil.

Oxidation of fats and oils is a free radical reaction (with the fat or oil being R):

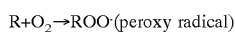

$R+O_2 \rightarrow ROO\cdot$ (peroxy radical)

The peroxy radicals can propagate producing many more oxygenated free radical molecules that decompose to form compounds, which have color and odor (for example but not limited to ketones, aldehydes and alcohols, among others). When an antioxidant is present, the peroxy radical, after the initiation step, reacts with the antioxidant terminating the free radical and preventing oxidation of the fat/oil from proceeding. The prevention of oxidation is useful for the stabilization of organic matter including, but not limited to, human dietary supplements, animal dietary supplements, edible oils, cosmetics, and plastics. The present invention comprises the use of kombic acid as such an antioxidant.

Kombic acid is a natural terpenoid consisting of a polyisoprenoic system joined to a resorcinol nucleus with a carboxyl group at the end of the polyisoprenoic hydrocarbon chain with the structure shown in FIG. 1. The chemical name for kombic acid is 16(2',5'-dihydroxy-3'-methylphenyl)-2,6,10,14-tetramethyl-2,6,10,14-hexadecatetraenoic acid. The invention further provides derivatives of this structure. These derivatives are shown in FIG. 2, where R' can be acyl moieties including, but not limited to acetyl-, butyryl-, succinyl-, nicotinyl- (or hydrogen for one R') and R" can be alkyl moieties including, but not limited to methyl, ethyl and longer alkyl chains.

The present invention teaches the use of kombic acid and its derivatives as antioxidants in: dietary supplements, or as a vitamin-like supplement in human food and/or animal feed; as an antioxidant/stabilizer for cosmetic and personal care formulations; as stabilizers against the oxidative degradation of high polymer systems (thermoplastic and thermosetting plastics); and in the stabilization of edible oils such as soybean, sunflower seed, canola, cottonseed and others, against the development of color, odor and rancidity caused by, but not limited to, the adverse effects of heat, light, and oxygen.

Processes for Isolating Kombic Acid

Vegetable oils have traditionally been separated from oilseeds by two methods: mechanical crushing and attendant oil expelling and solvent extraction. In the early days of solvent extraction, a variety of solvents were tested, but hexane has been the commercial solvent of choice for a half-century. Other solvents that have been investigated include halogenated hydrocarbons, acetone, alcohols and supercritical $CO_2$. While these other solvents can serve as oilseed extractants in place of hexane, economics, safety and yields have resulted in the choice of hexane as the standard.

The results of mechanical pressing and oil expelling and extraction by solvents is the same; the separation of saponifiable "oil" (triglycerides, diglycerides, monoglycerides and free fatty acids) from other parts of the oilseed, such as protein and fiber. Also carried along in the extraction are minor constituents that are unsaponifiable.

By conventional wisdom, kombic acid would be expected to have the same alcohol and supercritical $CO_2$ solubility as would a more common fatty acid such as palmitic or myristic acid. However, the invention methods described herein indicate that this is not the case. The present invention utilizes the heretofore-unrecognized fact that kombic acid has a different alcohol and supercritical $CO_2$ solubility from the more common fatty acids and thus can be separated from them. Significantly, these invention methods are economically adaptable for commercial manufacturing. Indeed, supercritical $CO_2$ extraction is a commonly used industrial method to decaffeinate coffee. In contrast, because the prior art has not recognized that kombic acid can be extracted from kombo butter based on alcohol and supercritical $CO_2$ solubility differences, a chromatography procedure was used[7]; chromatography is not adaptable for practical, economic commercial manufacturing.

Kombo butter is the crude vegetable oil obtained by mechanical crushing or by hexane extraction of the seed of the kombo nut that is native to West Central Africa. It contains various glycerides and free fatty acids (mostly myristic and myristoleic). It also contains the substituted palmitic fatty acid known as kombic acid. Unlike palmitic acid, however, kombic acid can be separated from the other fatty acids using alcohol or supercritical $CO_2$ extraction methods. These solvents remove the conventional glycerides and fatty acids leaving the kombic acid undissolved and thus made available for conventional further isolation techniques. The following examples illustrate the purification of kombic acid from kombo butter.

EXAMPLE 1
Purification of Kombic Acid By Liquid-Liquid Extraction

An alcohol extraction of crude kombo butter was made with 85% ethanol (15% water). This yielded 80+% kombic acid. The diluted alcohol was mixed with the solid kombo butter and agitated at ambient temperature until the butter was a fine granular solid and the alcohol layer was dark red. The alcohol was separated from the butter by filtration over sodium sulfate and the alcohol and water evaporated. Other conventional inorganic salt drying agents can also be used in place of sodium sulfate, for example, but not limited to calcium chloride. Alcohol percentage can vary from at least 70% to 100%. Methanol and isopropanol can also be used for extraction. The butter to alcohol ratio can vary from about 1:1 to at least about 1:5, with a ratio of about 1:3 being the most favorable.

EXAMPLE 2
Purification of Kombic Acid By Supercritical-Fluid Extraction

A sample of alcohol-extracted kombo butter (76% kombic acid) was charged to an extraction vessel, and gas at selected pressure and temperature conditions was passed through the vessel for a period of time. The high pressure stream of gas plus extracted material was passed through a pressure reduction valve into a collection vessel (glass U-tube or filter flask) where the extractables precipitate. The atmospheric gas exited the U-tube and flowed through the extraction vessel, the U-tube was removed. The conditions can be changed and the procedure can be repeated to collect multiple extracts from the same initial charge, until the extractable material is depleted. Alternatively, all the extracted material can be collected in one fraction. Finally the material remaining in the extraction vessel was collected post extraction. In this particularly example there was no residual material.

The relevant weights and observations from the test are summarized below:
Test: Hume-1 (76% kombic acid)
Charge: 7.45 g brown liquid

| Fraction # | Wt. Collected (g) | Observations | % Kombic Acid |
|---|---|---|---|
| HUME-1-1 | 1.06 | Pale yellow solids | 3 |
| HUME-1-2 | 0.73 | Orange liquid | 6 |
| HUME-1-3 | 0.72 | Brown liquid | 47 |
| HUME-1-4 | 1.27 | Brown liquid | 99 |
| HUME-1-5 | 3.60 | Brown liquid | 95 |
| | Sum = 7.38 | | |

Material balance=99.1%
The same extraction can be carried out on crude kombo butter to give fractions of similar high purity with respect to kombic acid.

The purified kombic acid can then be derivatized. The kombic acid derivatives encompassed by the instant invention include, but are not limited to, a methyl ester of kombic acid, a diacetate, a dimethyl ether, a quinone and a primary alcohol, as well as those derivatives illustrated by FIG. 2. Such kombic acid derivatives are prepared using standard organic chemical preparative techniques known to those of skill in the art. These derivatives are usable as antioxidants either alone or in combination with kombic acid.

The following examples provide means for characterizing the purified kombic acid or kombic acid derivatives following purification and/or derivitization.

EXAMPLE 3
Analytical Methods for Characterization of Kombic Acid: Gas Chromatography/Flame Ionization Detector 0.01 g of kombic acid was esterified with 1.0 ml of a mixture containing 1 part trimethylchlorosilane, 3 parts hexamethyldisilazane and 9 parts pyridine for a reaction time of 15 minutes at ambient temperature. The esterified sample trimethylsilicate ester was analyzed as follows using a Hewlett Packard 6890 Capillary Gas Chromatograph with Flame Ionization Detector.

Injection: 2.0 $\mu l$

Injector Temp: 275 C.

Split ratio: 1:50

Detector Temp: 300 C.

Flow: Constant pressure at 12 PSI

Oven Temp program: Initial 240 C. for 2 min., ramp at 10 C. per min. to 270 C., and hold for 25 min (Peak retention time at approximately 22 min.) The purity as determined by percent area=81% kombic acid EXAMPLE 4
Analytical Methods for Characterization of Kombic Acid: High Performance Liquid Chromatography The High Performance Liquid Chromatography method included a direct injection (5 $\mu l$) of diluted kombic acid (0.01 g in 10.0 ml alcohol) per the following parameters. The mobile phase was 70% acetonitrile: 20% methanol: 10% buffer (0.1% phosphoric acid in water), using a UV Detector at 280 nm, and a C18 Reverse Phase Column at 40 C with flow of 0.9 ml./min. The peak retention time was approximately 3 min.

The Use of Kombic Acid and its Derivatives as an Antioxidant

Some antioxidant compounds, such as the example of the present invention, contain extensive polyunsaturation (in this case polyisoprenoic structure) with allylic carbon atoms adjacent to the unsaturation. An allylic structure is shown below:

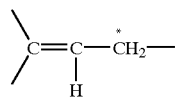

The starred carbon atom is an allylic carbon. The sites very easily form hydroperoxides and peroxides as part of the propagation reaction when fats and oils oxidize and form reactive chains. The multiplicity of allylic sites on kombic acid and similar antioxidants in effect act as chain stoppers for fat and oil oxidation reactions and thus limit the amount of oxidation occurring in the fat or oil. There are a very unusually high number of allylic carbons in each molecule of kombic acid or kombic acid derivative, eleven in all. The hydroxyl groups on the benzene ring also act as chain stoppers as well, thus enhancing the antioxidant power of kombic acid.

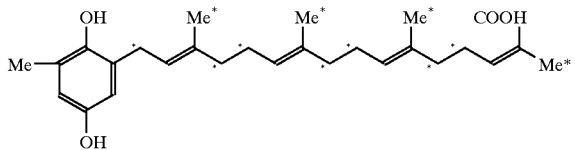

It is not known, a priori, that a particular compound can function as an antioxidant. Indeed, in the paper discussing the original isolation of kombic acid[7], no mention of a use for kombic acid is made. Indeed, several possible uses for kombic acid have been postulated including its use as an antifungal agent against thrush[9]. It is important to note that none of the uses postulated thus far include the use of kombic acid as an antioxidant.

The instant invention is based on the heretofore-unrecognized function of kombic acid as an antioxidant.

The following examples show lipid peroxidation antioxidant activity of kombic acid. They are in vitro simulations of how kombic acid would function in the human body as an antioxidant as a dietary supplement and food ingredient. These experiments use α-tocopherol (Vitamin E) as a standard. Natural vitamin E (d-α-tocopherol) has a long history of benefits in human nutrition. In addition to epidemiologic studies that suggest a benefit for high intakes of α-tocopherol, studies of supplementation in humans have clearly shown that α-tocopherol decreases lipid peroxidation, platelet aggregation, and functions as a potent anti-inflammatory agent. In the five large prospective clinical trials with α-tocopherol therapy, four have shown a beneficial effect on cardiovascular end-points. Cardiovascular end-points include heart attack, and evidence of coronary artery disease from angiograms and/or EKG testing. An antioxidant superior or equivalent to vitamin E in experimental tests simulating the human biological system is a unique and valuable discovery as not many of the vast array of organic chemicals have any power as antioxidants at all.

EXAMPLE 5

In Vitro Simulation of Protection of the Human System Against Oxidation by Kombic Acid and/or a Kombic Acid Derivative Using Rat Liver Microsomes Rat liver microsomes, previously incubated with or without inhibitor, were treated with ascorbic acid and ferrous sulfate to induce lipid peroxidation. The extent of lipid peroxidation was determined by the amount of malondialdehyde produced, which was determined by reaction with thiobarbituric acid.

Biological specimens contain a mixture of thiobarbituric acid reactive substances (TBARS), including lipid hydroperoxides and aldehydes, which increase as a result of oxidative stress. TBARS return to normal levels over time, depending upon the presence of antioxidants. In practice, TBARS are expressed in terms of malondialdehyde (MDA) equivalents. In this assay, an MDA standard is used to construct a standard curve against which unknown samples can be plotted.

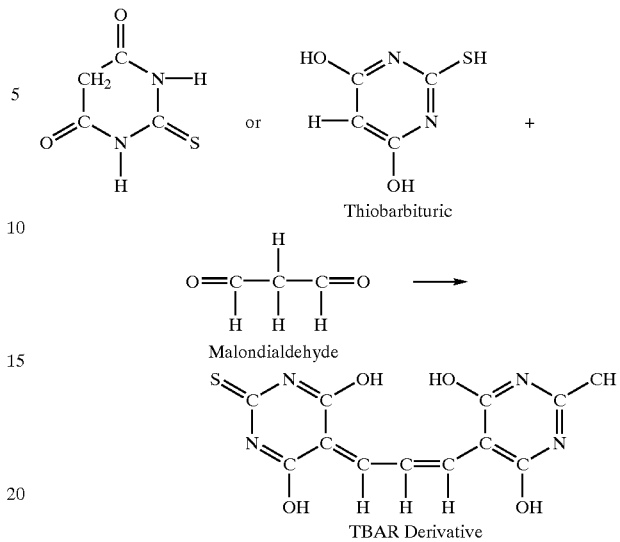

The presence of this compound is measured by fluorometry or spectrophotometry.

| Inhibitor | Results: Inhibitor concentration (µg/mL) | | |
|---|---|---|---|
| | 0.625 | 0.313 | 0.156 |
| Kombic Acid (ECC antiox 001) | | | |
| Inhibition ratio* | 0.10 | 0.11 | 0.64 |
| % Inhibition | 90% | 89% | 36% |
| $IC_{50}$** | | | 0.20 µg/mL |
| (+/-)-α-tocopherol (synthetic vitamin E) | | | |
| Inhibition ratio* | 0.34 | 0.50 | 0.92 |
| % Inhibition | 66% | 50% | 8% |
| $IC_{50}$** | | | 0.31 µg/mL |

*The amount of peroxidation (nmoles of MDA produced) in the presence of inhibitor divided by the amount of peroxidation in the absence of inhibitor.
**The concentration required to inhibit lipid peroxidation by 50%, obtained by plotting. Lower values indicate better antioxidant activity.

The results of this example show that kombic acid demonstrates very strong antioxidant activity. It is consistently better than vitamin E on a weight basis. Given that the molecular weights of kombic acid and α-tocopherol are approximately the same, 426 and 462 respectively, kombic acid is a consistently better antioxidant than α-tocopherol (vitamin E) on a molar basis.

In addition, kombic acid derivatives, including, but not limited to, the methyl ester of kombic acid, a diacetate, a quinone and a primary alcohol of kombic acid will show similar protection against oxidation as the underivatized kombic acid does in this experiment.

EXAMPLE 6

In Vitro Simulation of Protection of the Human System Against Oxidation by Kombic Acid and/or a Kombic Acid Derivative Using Human Low Density Lipoprotein Human low density lipoprotein was dialyzed, incubated with or without inhibitor, and then treated with 10 µM copper to induce lipid peroxidation for several hours. The extent of lipid peroxidation was determined by the amount of malondialdehyde produced, which was determined by reaction with thiobarbituric acid as described above.

Results:

| Inhibitor | $IC_{50}$: data ($\mu M$) | $IC_{50}$: mean +/- Standard Deviation |
|---|---|---|
| Kombic Acid (ECC antiox 001) | 7.8, 2.1, 2.2, 8.5, 5.2 | 5.2 +/- 2.7 $\mu M$ |
| (+)-α-tocopherol, 99% (natural vitamin E) | 5.1, 3.5, 5.1 | 4.6 +/- 0.75 $\mu M$ |

$IC_{50}$ = The concentration required to inhibit LDL lipid peroxidation by 50%, obtained by plotting concentration against activity. Lower values indicate better activity.

This example shows that there is no significant difference in antioxidant activity between kombic acid and natural vitamin E; they are statistically equivalent in power. In addition, synthetic vitamin E (+/−) was found to inhibit peroxidation equally as well as natural (+) vitamin E. Again, it should be noted that an antioxidant superior or equivalent to vitamin E in experimental tests simulating the human biological system is a unique and valuable discovery as not many of the vast array of organic chemicals have any power as antioxidants at all.

Kombic acid derivatives, including, but not limited to, the methyl ester of kombic acid, a diacetate, a quinone and a primary alcohol of kombic acid will a show similar protection against oxidation as the underivatized kombic acid does in this experiment.

EXAMPLE 7
Stabilization of Edible Oils Using Kombic Acid and/or a Kombic Acid Derivative The Oxygen Stability Index is used to measure the effectiveness of antioxidants in the stabilization of edible oils against oxidative degradation. The "Hours to end-point" indicate when a time/conductivity curve changes shape, with a sharp slope upturn at that time point. The temperature of the test, which measures conductivity of a solution into which oxidation products from the oil being tested is passed, is 110° C.

| Oil (soybean) | Hours to end-point |
|---|---|
| Control | 5.65, 5.70, 5.75, 5.85 |
| Control + 40 ppm kombic acid | 8.35, 8.85 |
| Control + 300 ppm kombic acid | 15.55, 15.40 |
| Control + 200 ppm TBHQ*** | 21.10, 19.85 |

***TBHQ = tributyl-tert-hydroquinone is a commercial synthetic antioxidant. IN this experiment, both kombic acid and TBHQ are effective antioxidants, albeit at different levels. However, TBHQ is a synthetic antioxidant. Because it is synthetic, the amount that can be used in food, for example to stabilize an edible oil, is limited by the FDA to 200 ppm. In contrast, kombic acid is a natural antioxidant. Therefore, the FDA may approve its use in foods at a higher level than 200 ppm. This experiment shows that kombic acid, although not quite as effective as the synthetic TBHQ, is still an effective antioxidant at levels that are FDA approvable.

EXAMPLE 8
Stabilization of Plastics by Kombic Acid and/or a Kombic Acid Derivative Plastics can be formulated to contain a specific amount of kombic acid, or a kombic acid derivative such as, but not limited to the methyl ester of kombic acid, diacetate, quinone, and a primary alcohol. As a control, these same plastics can be formulated without kombic acid (or without a kombic acid derivative). As a further control, these plastics can be formulated to contain a synthetic antioxidant compound, for example, but not limited to TBHQ. These plastics can then be exposed to heat, light and air oxidation. An analysis of color, and odor development can then be made. Plastics formulated with kombic acid will be more resistant to color and odor development than the plastics not containing kombic acid. Plastics formulated with a kombic acid derivative will also be more resistant to color and odor development than the plastics not containing the kombic acid derivative. Furthermore, the plastics containing kombic acid or a kombic acid derivative will be either the same or more resistant to color and odor development than those plastics formulated with the synthetic antioxidant.

EXAMPLE 9
Stabilization of Cosmetics by Kombic Acid and/or a Kombic Acid Derivative Cosmetics can be formulated to contain a specific amount of kombic acid, or kombic acid derivative such as, but not limited to a methyl ester of kombic acid, a diacetate, a quinone and a primary alcohol. As a control, these same cosmetics can be formulated without kombic acid (or without a kombic acid derivative). As a further control, these cosmetics can be formulated to contain a synthetic antioxidant compound, for example, but not limited to TBHQ. These cosmetics can then be exposed to heat, light and air oxidation. An analysis of color, and odor development can then be made. Cosmetics formulated with kombic acid will be more resistant to color and odor development than the plastics not containing kombic acid. Cosmetics formulated with a kombic acid derivative will also be more resistant to color and odor development than the cosmetics not containing the kombic acid derivative. Furthermore, the cosmetics containing kombic acid or a kombic acid derivative will be either the same or more resistant to color and odor development than those cosmetics formulated with the synthetic antioxidant.

All measurements disclosed herein are at standard temperature and pressure, at sea level on Earth, unless indicated otherwise. All materials used or intended to be used in a human being are biocompatible, unless indicated otherwise.

REFERENCES

1. Siemandi, H. et al., "The Effect of Cis-9-Cetyl Myristoleate (CMO) and Adjunctive Therapy on the Course of Arthritic Episodes in Patients with Various Auto-Immune Diseases Characterized by the Common Terminology, 'Arthritis' and "Psoriasis"', A Randomized Clinical Trial. *Townsend Letter for Doctors and Patients.*
2. R. R. Barathur, J. B. Bookout, S. Steevtsan, E. S. Freeland, R. L. Hesslink, Jr. "A Fatty Acid Ester Complex (CMC) Improves Quality of Life Outcomes in Osteoarthritis (OA) Patients" ClinCyte, 1055 Flintkote Ave., San Diego, Calif. 92121, Imagenetix, 16935 W. Bernardo Dr., San Diego, Calif. 92127,"To be published".
3. Mensier, P. H. (1957) *Dictionnaire des Huiles Vegetales.* Editions Paul Lechevalier. Paris.
4. Wijs. J. J. A. (1906) *Vetten, Olieen en Wassen* Koloniaal Museum, Haarlem.
5. Atherton, D. and Mcara, M. L. (1939) Chem. Ind. (London) 353.
6. Hilditch, T. P. and Williams, P. N. (1964) *The Chemical Constitution of Natural Fats.* Chapman & Hall, London.
7. Lok, C. M., Groenewegen, A., Stroink, B. A., and Ward, J. P. *Phytochemistry* 22(9) 1973–1976 (1983).

8. Omobuwajo, O. R., Adesanya, S. A., Babalola, G. O Phystochemistry 31, 1013 (1992).
9. U.S. Pat. No. , 5,674,900.

The foregoing embodiments are presented by way of example only; the scope of the present invention is to be limited only by the following claims.

What is claimed is:

1. An antioxidant comprising kombic acid that is useful in prolonging the shelf life of food items and vitamin-mineral supplements that are susceptible to rancidity, the antioxidant being mixed with a food item or supplement to form a dietary mixture thereof.

2. An antioxidant comprising kombic acid that is useful in prolonging the shelf life of cosmetic and personal care items that are susceptible to rancidity, the antioxidant being mixed with a cosmetic or personal care item.

3. An antioxidant comprising kombic acid that is useful in prolonging the shelf life of an edible oil that is susceptible to rancidity, the antioxidant being mixed with said edible oil.

4. The antioxidant of claim 3, wherein said edible oil is selected from the group consisting of soybean, sunflower seed, canola, and cottonseed.

5. The antioxidant of claim 1, 2, or 3, wherein said kombic acid is a derivative of kombic acid.

6. The antioxidant of claim 5, wherein said derivative of kombic acid is selected from the group consisting of the methyl ester of kombic acid, the diacetate of kombic acid, the quinone of kombic acid and a primary alcohol of kombic acid.

7. An antioxidant comprising a compound of the formula:

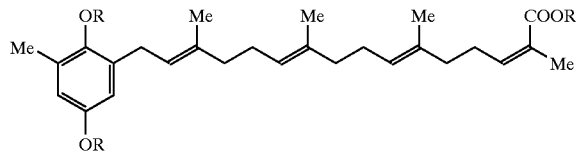

wherein R' represents an acyl group or a hydrogen; and R" represents hydrogen or an alkyl group or its salt, useful in prolonging the shelf life of food items and vitamin-mineral supplements that are susceptible to rancidity, the antioxidant being mixed with a food item or supplement to form a dietary mixture thereof.

8. An antioxidant comprising a compound of the formula:

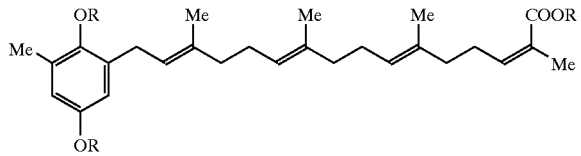

wherein R' represents an acyl group or a hydrogen; and R" represents hydrogen or an alkyl group or its salt, useful in prolonging the shelf life of cosmetic and personal care items that are susceptible to rancidity, the antioxidant being mixed with a cosmetic or personal care item.

9. An antioxidant comprising a compound of the formula:

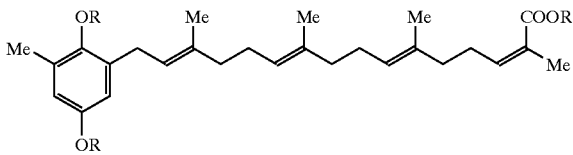

wherein R' represents an acyl group or a hydrogen; and R" represents hydrogen or an alkyl group or its salt, useful in prolonging the shelf life of an edible oil that is susceptible to rancidity, the antioxidant being mixed with said edible oil.

10. The compound of claim 9, wherein said edible oil is selected from the group consisting of soybean, sunflower seed, canola, and cottonseed.

11. The compound of claim 7, 8, or 9 wherein said acyl group is selected from the group consisting of acetyl, butyryl, succinyl, nicotinyl.

12. The compound of claim 7, 8, or 9 wherein said alkyl group is selected from the group consisting of methyl and ethyl.

13. A method of preventing oxidation of organic materials comprising adding to said materials an effective amount of kombic acid.

14. The method of claim 13, wherein said kombic acid is a derivative of kombic acid.

15. The method of claim 14, wherein said derivative of kombic acid is selected from the group consisting of the methyl ester of kombic acid, the diacetate of kombic acid, the quinone of kombic acid and a primary alcohol of kombic acid.

16. The method of claim 13, wherein said organic materials is selected from the group consisting of human dietary supplements, animal dietary supplements, edible oils, cosmetics, and plastics.

17. A method for the preparation of an antioxidant for organic materials comprising the steps of:
    (a) mixing crude kombo butter with a dilute alcohol to form a mixture of kombo butter and alcohol;
    (b) agitating said mixture;
    (c) allowing said mixture to separate into component alcohol layer and solid layer;
    (d) separating said alcohol layer from said solid layer by filtration over an inorganic salt drying agent; evaporating said alcohol layer to recover said antioxidant.

18. The method of claim 17, wherein said inorganic salt drying agent is sodium sulfate.

19. The method of claim 17, wherein said alcohol is selected from the group consisting of ethanol, methanol, and isopropanol.

20. The method of claim 17, wherein said mixture of kombo butter and alcohol is in a ratio of from about 1 part kombo butter to from about 1 part to about 5 parts dilute alcohol.

21. The method of claim 17, wherein said mixture of kombo butter and alcohol is in a ratio of about 1 part kombo butter to about 3 parts dilute alcohol.

22. The method of claim 17, wherein said dilute alcohol is comprised of at least 70% alcohol.

23. The method of claim 17, wherein said antioxidant is kombic acid.

24. The method of claim 17, wherein said antioxidant is a kombic acid derivative.

25. The method of claim 24, wherein said kombic acid derivative is selected from the group consisting of the methyl ester of kombic acid, the diacetate of kombic acid, the quinone of kombic acid and a primary alcohol of kombic acid.

26. A process for obtaining kombic acid suitable for use as an antioxidant comprising:
   (a) extracting kombo butter with a polar solvent to obtain an extract containing polar compounds including kombic acid;
   (b) contacting said extract with an adsorbent material having an affinity for apolar compounds for adsorbing the kombic acid to separate the kombic acid from the apolar compounds of the extract;
   (c) evaporating said polar solvent from the kombic acid to obtain a residue containing said kombic acid.

27. The process of claim 26 wherein said polar solvent is an alcohol.

28. The process of claim 27, wherein said alcohol is selected from the group consisting of ethanol, methanol, and isopropanol.

29. The process of claim 27, wherein said alcohol is at least 70% alcohol.

30. The process of claim 26, wherein said extraction of kombo butter with a polar solvent is at a ratio of from at least about 1 part kombo butter and 1 part polar solvent, to about 1 part kombo butter and about 5 parts polar solvent.

31. The process of claim 26, wherein said extraction of kombo butter with a polar solvent is at a ratio of about 1 part kombo butter to about 3 parts polar solvent.

32. A method for the preparation of an antioxidant for organic materials which comprises the steps of:
   (a) charging a sample of kombo butter to an extraction vessel;
   (b) selecting pressure and temperature conditions of a gas to pass through said vessel for a period of time said pressure and temperature conditions allowing said gas to extract kombic acid out from said kombo butter;
   (c) passing said mixture of said gas and said kombic acid through a pressure reduction valve into a collection vessel causing extractables to precipitate;
   (d) collecting post extraction material, said post extraction material comprising purified kombic acid.

33. The method of claim 32, wherein said kombo butter is selected from the group consisting of alcohol-extracted kombo butter and crude kombo butter.

* * * * *

UNITED STATES PATENT AND TRADEMARK OFFICE
CERTIFICATE OF CORRECTION

PATENT NO.   : 6,489,494 B1
DATED        : December 3, 2002
INVENTOR(S)  : Edward C. Leonard It is certified that error appears in the above-identified patent and that said Letters Patent is hereby corrected as shown below:

Column 11,
Lines 36-40, the formula of Claim 7 should read:

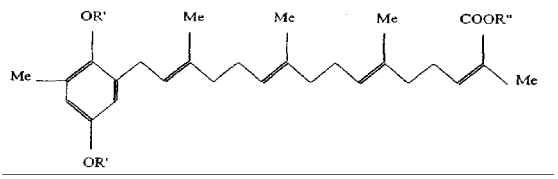

Lines 54-59, the formula of Claim 8 should read:

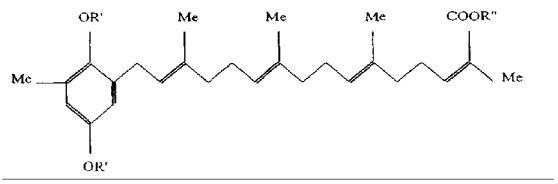

Column 12,
Lines 3-7, the formula of Claim 9 should read:

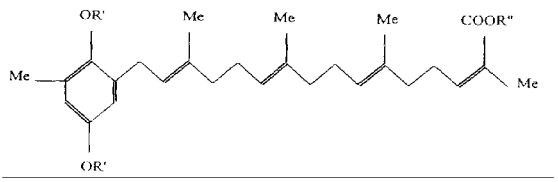

Signed and Sealed this

Thirteenth Day of July, 2004

JON W. DUDAS
*Acting Director of the United States Patent and Trademark Office*